(12) United States Patent
Rudser

(10) Patent No.: US 11,131,968 B2
(45) Date of Patent: Sep. 28, 2021

(54) PUMP MOTOR CONTROL WITH ADAPTIVE STARTUP

(71) Applicant: HeartWare, Inc., Miami Lakes, FL (US)

(72) Inventor: John Rudser, Miami, FL (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 16/910,509

(22) Filed: Jun. 24, 2020

(65) Prior Publication Data

US 2020/0319607 A1 Oct. 8, 2020

Related U.S. Application Data

(63) Continuation of application No. 15/391,997, filed on Dec. 28, 2016, now Pat. No. 10,732,583.

(Continued)

(51) Int. Cl.
*G05B 13/02* (2006.01)
*G05B 23/02* (2006.01)
(Continued)

(52) U.S. Cl.
CPC ......... *G05B 13/021* (2013.01); *A61M 60/148* (2021.01); *A61M 60/50* (2021.01);
(Continued)

(58) Field of Classification Search
CPC .............. G05B 13/021; G05B 23/0294; G05B 2219/41018; H02P 1/16; H02P 6/20;
(Continued)

(56) References Cited

U.S. PATENT DOCUMENTS 4,137,913 A * 2/1979 Georgi .............. A61M 5/14216
128/DIG. 12
5,711,753 A 1/1998 Pacella et al.
(Continued)

FOREIGN PATENT DOCUMENTS

WO 1999017819 A1 4/1999

OTHER PUBLICATIONS

International Search Report and Written Opinion dated Apr. 10, 2017, for corresponding International Application No. PCT/US2016/068817; International Filing Date: Dec. 28, 2016 consisting of 10 Pages.

*Primary Examiner* — Muhammad S Islam
*Assistant Examiner* — Devon A Joseph
(74) *Attorney, Agent, or Firm* — Christopher & Weisberg, P.A.

(57) ABSTRACT

An apparatus for starting operation of a motor of an implantable blood pump including a memory storing one or more default parameters for at least one of controlling and monitoring the startup operation. A processor operatively coupled to the motor is included, the processor is configured to: commence the startup operation based on the one or more default parameters; detect an error during the startup operation; adjust at least one of the one or more default parameters in response to the detected error; store the at least one adjusted parameter in the memory; and commence subsequent startup operations based at least in part on the at least one adjusted parameter.

18 Claims, 7 Drawing Sheets

Related U.S. Application Data

(60) Provisional application No. 62/271,618, filed on Dec. 28, 2015.

(51) Int. Cl.

| | | |
|---|---|---|
| *H02P 1/16* | (2006.01) | |
| *H02P 6/20* | (2016.01) | |
| *A61M 60/50* | (2021.01) | |
| *A61M 60/148* | (2021.01) | |
| *A61M 60/871* | (2021.01) | |

(52) U.S. Cl.
CPC ....... *A61M 60/871* (2021.01); *G05B 23/0294* (2013.01); *H02P 1/16* (2013.01); *H02P 6/20* (2013.01); *A61M 2205/16* (2013.01); *A61M 2205/3331* (2013.01); *A61M 2205/3365* (2013.01); *A61M 2205/50* (2013.01); *A61M 2205/52* (2013.01); *G05B 2219/41018* (2013.01)

(58) Field of Classification Search
CPC .... A61M 1/1086; A61M 1/127; A61M 1/122; A61M 2205/52; A61M 2205/50; A61M 2205/16; A61M 2205/3365; A61M 2205/3331
See application file for complete search history.

(56) References Cited

U.S. PATENT DOCUMENTS

| | | | |
|---|---|---|---|
| 7,645,225 B2 | 1/2010 | Medvedev et al. | |
| 7,972,122 B2 | 7/2011 | LaRose et al. | |
| 8,007,254 B2 | 8/2011 | LaRose et al. | |
| 8,419,609 B2 | 4/2013 | Shambaugh, Jr. et al. | |
| 8,506,470 B2 | 8/2013 | LaRose et al. | |
| 8,512,013 B2 | 8/2013 | LaRose et al. | |
| 8,975,845 B2 * | 3/2015 | Guzelgunler | H02P 1/46 318/400.22 |
| 9,511,179 B2 | 12/2016 | Casas et al. | |
| 9,623,161 B2 * | 4/2017 | Medvedev | A61M 60/50 |
| 9,629,948 B2 * | 4/2017 | Schade | A61M 60/422 |
| 9,849,224 B2 * | 12/2017 | Angwin | A61M 60/871 |
| 10,075,107 B2 * | 9/2018 | Lepka | H02P 29/0241 |
| 10,117,983 B2 * | 11/2018 | Medvedev | F04D 29/22 |
| 2001/0037093 A1 * | 11/2001 | Benkowski | A61M 60/422 604/288.01 |
| 2003/0069465 A1 * | 4/2003 | Benkowski | A61M 60/422 600/16 |
| 2005/0215843 A1 * | 9/2005 | Medvedev | A61M 60/50 600/16 |
| 2006/0193090 A1 * | 8/2006 | Ho | H02P 21/141 361/23 |
| 2011/0178361 A1 * | 7/2011 | Yomtov | A61M 60/40 600/16 |
| 2012/0245681 A1 * | 9/2012 | Casas | A61M 60/50 623/3.28 |
| 2013/0106331 A1 * | 5/2013 | Guzelgunler | H02P 1/46 318/400.21 |
| 2014/0241904 A1 * | 8/2014 | Yanai | F04D 1/00 417/53 |
| 2014/0340008 A1 * | 11/2014 | Reynolds | H02P 1/52 318/400.11 |
| 2014/0357937 A1 * | 12/2014 | Reyes | A61M 60/50 600/17 |
| 2015/0202448 A1 * | 7/2015 | Hoffer | A61B 5/4836 607/42 |
| 2015/0290376 A1 * | 10/2015 | Schade | A61M 1/122 600/16 |
| 2016/0058929 A1 * | 3/2016 | Medvedev | A61M 60/50 600/17 |
| 2016/0061207 A1 * | 3/2016 | Penn, II | F04B 49/06 417/44.1 |
| 2017/0136163 A1 * | 5/2017 | Medvedev | F04D 15/0066 |

\* cited by examiner

PUMP MOTOR CONTROL WITH ADAPTIVE STARTUP

CROSS-REFERENCE TO RELATED APPLICATION

This application is a continuation of U.S. patent application Ser. No. 15/391,997, filed Dec. 28, 2016 and is related to and claims priority to U.S. Provisional Patent Application Ser. No. 62/271,618, filed Dec. 28, 2015, entitled PUMP MOTOR CONTROL WITH ADAPTIVE STARTUP, the entirety of which is incorporated herein by reference.

STATEMENT REGARDING FEDERALLY SPONSORED RESEARCH OR DEVELOPMENT n/a

TECHNICAL FIELD

The present invention relates to a method and system for adjusting operational parameters of a motor of an implanted medical device.

BACKGROUND

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as ventricular assist device or "VAD."

A VAD is a device which is used to assist the heart of a mammalian subject such as a human patient. A typical VAD includes a pump which is implanted in the body of the subject. The pump typically has an inlet connected to a source of blood to be circulated, and an outlet connected to an artery. Most typically, the inlet of the pump is connected to the interior of the left ventricle and the outlet of the pump is connected to the aorta, so that the pump operates in parallel with the left ventricle to impel blood into the aorta. The pump may be a miniature rotary impeller pump having an impeller disposed in a pump housing and driven in rotation by a small electric motor which may be closely integrated with the pump. The motor in turn typically is powered by an implantable power source such as a storage battery with an arrangement for charging the battery from an external power source. The VAD typically includes a control system which controls operation of the power source so as to drive the impeller at a set rotational speed and thus provide constant pumping action. VADs can be used to assist the heart of subjects suffering from conditions which impair the pumping ability of the heart. Such assistance can be provided permanently, or while the subject awaits a suitable heart transplant. In other cases, the assistance provided by the VAD allows the heart to heal.

Starting up operating of a rotary pump, such as the rotary impeller pump of a VAD, may be difficult, particularly when the rotor is at rest up against the housing of the pump. Where the rotary pump is off and/or temporarily ceases operation, it is desirable to be able to start or resume operation of the pump as quickly and as efficiently as possible so as to provide assistance to the subject's heart. However, ramping the speed of the pump's rotor too quickly can be counterproductive. For instance, if the pump speed is increased too quickly, it can result in phase commutation errors. Further, it can create suction within the subject's ventricle, wherein the ventricle is collapsed and essentially devoid of blood. This condition may in turn cause the flow rate of blood through the pump to decline rapidly and to the extent that the flow rate is insufficient, the pump cannot provide sufficient circulatory assistance to the subject. Thus, these conditions are undesirable.

Additionally, ramping the speed of a pump requires a supply of power to be provided to the pump. However, supplying too much power too quickly may cause the control electronics to overheat. Aside from any safety hazards associated with overheating of control circuitry, in many cases, such overheating can also trigger a cutoff, which in turn hinders the controller's ability to start up or resume operation of the pump. Thus, this scenario is also undesirable.

SUMMARY

The present invention advantageously provides for an apparatus for starting operation of a motor of an implantable blood pump including a memory storing one or more default parameters for at least one of controlling and monitoring the startup operation. A processor operatively coupled to the motor is included, the processor is configured to: commence the startup operation based on the one or more default parameters; detect an error during the startup operation; adjust at least one of the one or more default parameters in response to the detected error; store the at least one adjusted parameter in the memory; and commence subsequent startup operations based at least in part on the at least one adjusted parameter.

In another aspect of this embodiment, the error detected during the startup operation is a failure to start the motor.

In another aspect of this embodiment, storing the at least one adjusted parameter in the memory occurs when commencing subsequent startup of the motor is successful.

In another aspect of this embodiment, the error detected during the startup operation is indicative that the motor is operating as a result of the startup but not in a desired manner.

In another aspect of this embodiment, the error detected during the startup operation is indicative that the motor is operating as a result of the startup but an at least one of an undesirable operational error and a condition occurred during the startup.

In another aspect of this embodiment, the memory stores parameter adjustment data indicating an association between at least one error type of the detected error and at least one associated parameter, and wherein the processor is configured to identify at least one default parameter associated with the detected error based on the parameter adjustment data and to adjust the at least one default parameter in response to the detected error.

In another aspect of this embodiment, the parameter adjustment data further indicates whether to at least one of increase and decrease the associated parameter in response to the at least one error type to reduce the likelihood of a recurrence of the at least one error type, and wherein the processor is configured to at least one of increase and decrease the at least one default parameter based on the parameter adjustment data.

In another aspect of this embodiment, the processor is configured to ramp a speed of the motor based on at least one of the one or more default parameters, and phase lock the motor based on at least one of the one or more default parameters.

In another aspect of this embodiment, the processor is configured to detect an error during the startup operation based on at least one of a determined speed of the motor, current supplied to the motor, flow rate of blood through the pump, and pressure head exerted by the pump.

In another aspect of this embodiment, the one or more default parameters includes a value indicating a threshold number of errors, and wherein the processor is further configured to cease operation of the motor in response to registering the threshold number of errors during consecutive startup operation attempts.

In another aspect of this embodiment, the one or more default parameters includes at least one parameter related to a rate at which speed of the motor is ramped, and wherein the processor is configured to identify a suction condition at the implantable blood pump, and to adjust the at least one parameter related to a rate at which speed of the motor is ramped in response to the suction condition.

In another aspect of this embodiment, the one or more default parameters includes at least one parameter related to a rate at which speed of the motor is ramped, and wherein the processor is configured to identify a high pressure condition at the implantable blood pump, and to adjust the at least one parameter related to a rate at which speed of the motor is ramped in response to the high pressure condition.

In another aspect of this embodiment, the one or more default parameters includes at least one parameter related to motor phase control, and wherein the processor is configured to identify a commutation error at a rotor of the implantable blood pump, and to adjust the at least one parameter related to motor phase control in response to the commutation error.

In another embodiment, a method adaptively adjusting operational parameters of a motor of an implanted medical device includes commencing a startup operation based on one or more preset operational parameters. An error during the startup operation is detected. In response to the detected error at least one of the one or more preset operational parameters is adjusted. At least one of the one or more preset operational parameters is replaced with the at least one adjusted parameter as a default parameter in the memory. Subsequent startup operations based at least in part on the at least one adjusted parameter are commenced.

In another aspect of this embodiment, the detecting and adjusting are repeatedly performed until the startup operation is successfully completed.

In another aspect of this embodiment, the method further includes associating the detected error with at least one of the one or more present operational parameters based upon preset association data, and wherein adjusting at least one of the one or more preset operational parameters is based on the association.

In another aspect of this embodiment, the association further comprises an indication whether to at least one of increase and decrease the at least one of the one or more preset operational parameters, and wherein adjusting at least one of the one or more preset operational parameters comprises at least one of an increase and a decrease of the at least one of the one or more preset operational parameters based on the indication.

In another aspect of this embodiment, commencing a startup operation comprises ramping a speed of the motor based on at least one of the one or more preset operational parameters, and phase-locking the motor based on at least one of the one or more preset operational parameters.

In another aspect of this embodiment, when the motor is in an idle state, commencing a startup operation comprises aligning one or more stators of the motor with a predetermined position, and ramping a speed of the motor commences with the stators in the predetermined position.

In another aspect of this embodiment, detecting an error during the startup operation is based on at least one of a determined speed of the motor and current supplied to the motor.

In another aspect of this embodiment, the implanted medical device is a blood pump, and wherein detecting an error during the startup operation is based on at least one of a flow rate of blood through the pump, and pressure head exerted by the pump.

In another aspect of this embodiment, the method further includes registering an error in response detecting an error during the startup operation; clearing all registered errors in response to the startup operation being successfully completed; and ceasing operation of the motor in response to meeting a preset threshold number of registered errors.

In another aspect of this embodiment, the implanted medical device is a blood pump, wherein the detected error comprises one of a suction condition and a high pressure condition at the blood pump, and wherein a ramp operation of the motor is longer in duration using the adjusted parameter, as compared to the previous prior operational parameter.

In another aspect of this embodiment, the detected error comprises a commutation error, and wherein a parameter relating to a phase lock operation of the motor is adjusted in response to the commutation error.

In yet another embodiment, an apparatus for starting operation of a motor of an implantable blood pump a memory storing one or more default parameters for controlling or monitoring the startup operation includes a processor operatively coupled to the motor. The processor is configured to: commence the startup operation based on the one or more default parameters, the one or more default parameters includes a value indicating a threshold number of errors; ramp a speed of the motor based on at least one of the one or more default parameters, and phase lock the motor based on at least one of the one or more default parameters; detect an error during the startup operation, the error being at least one at least one of a determined speed of the motor, current supplied to the motor, flow rate of blood through the pump, and pressure head exerted by the pump; adjust at least one of the one or more default parameters in response to the detected error; store the at least one adjusted parameter in the memory; commence subsequent startup operations based at least in part on the at least one adjusted parameter; cease operation of the motor in response to registering the threshold number of errors during consecutive startup operation attempts. The memory is further configured to store parameter adjustment data indicating an association between at least one error type of the detected error and at least one associated parameter, the processor is further configured to identify at least one default parameter associated with the detected error based on the parameter adjustment data and to adjust the at least one default parameter in response to the detected error.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

The present disclosure provides for a routine that controls startup and subsequent operation of a motor. Such arrangement may be advantageous for implanted medical devices having a motor, such as the MVAD® Pump manufactured by HeartWare Inc. in Miami Lakes, Fla., USA. The MVAD® Pump is further discussed in, for example, U.S. Pat. Nos. 7,972,122, 8,007,254 and 8,419,609, the disclosures of which are hereby incorporated herein in their entirety.

Figure 1:
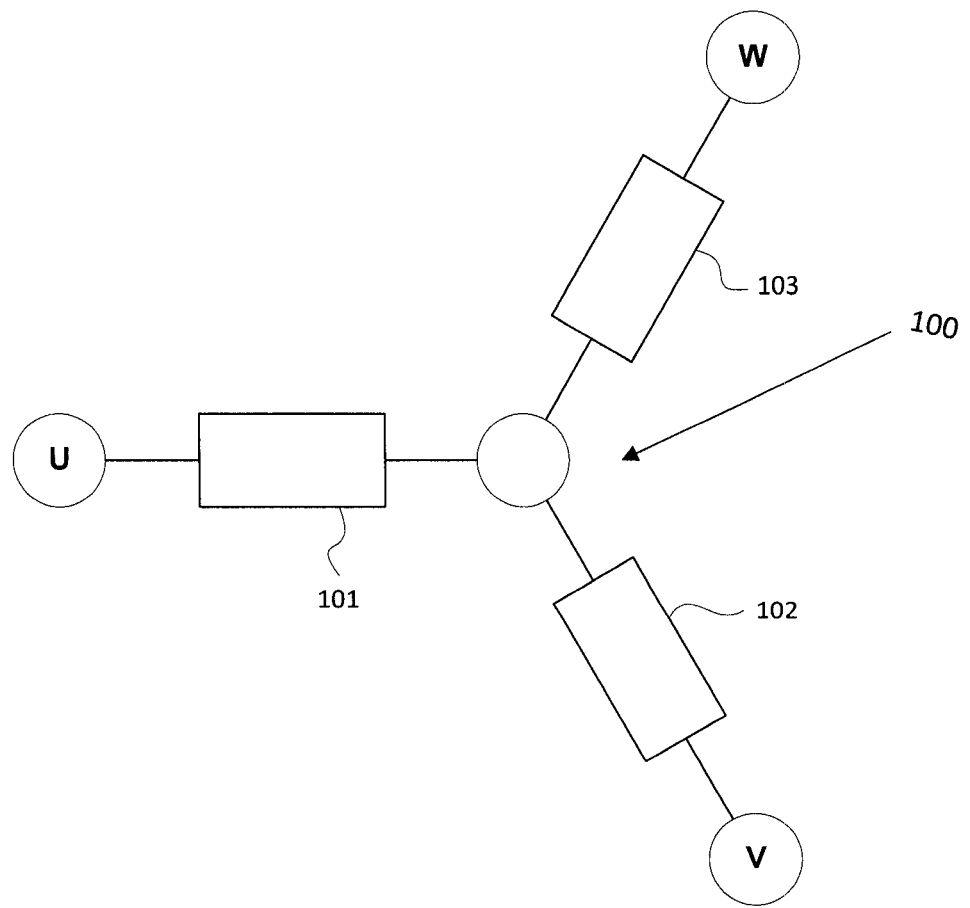
FIG. 1 is a schematic of an exemplary stator for a motor of an implantable blood pump constructed in accordance with the principles of the present application.
Figure 2:
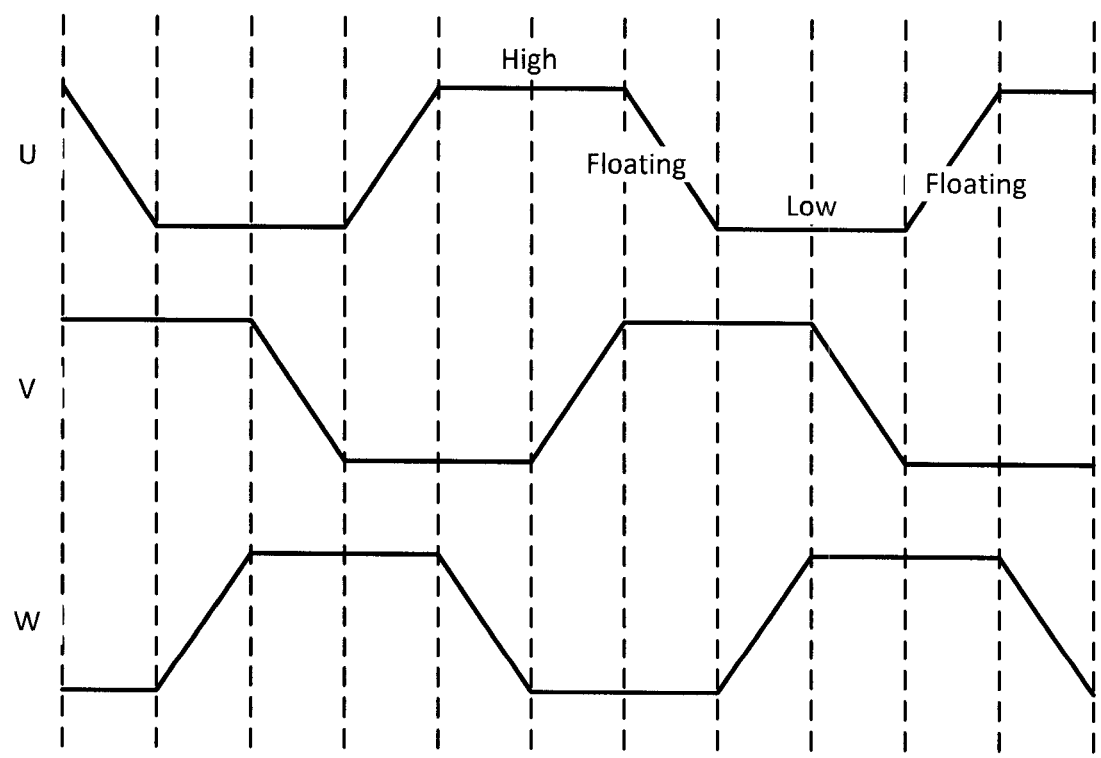
FIG. 2 is a chart showing the stator of FIG. 1 with a 6-sequence trapezoidal drive with commutation windows for each 60 degrees of electrical rotation of the rotor.

Now referring to the drawings in which like reference designators refer to like elements there is shown in FIG. 1 a sensorless three-phase brushless direct-current (BLDC) motor for an implantable blood pump constructed in accordance with the principles of the present application and designated generally as "100". Three-phase motor control may be realized in the BLDC motor by driving the three windings of the motor's stator. Each winding 101, 102, 103 of the stator may be controlled by a different phase U, V, W, respectively, of a three-phase power input. In one configuration, as shown in FIG. 2, the three-phase power input may be a 6-sequence trapezoidal drive with commutation windows for each 60 degrees of electrical rotation of the rotor. At a given time, one winding of the stator may be driven "high," a second driven "low," and a third left "floating" in that it is not being driven by the controller. In an exemplary configuration, three-phase BLDC motor control may be realized using a set of three half-bridge MOSFET switches. In such a configuration, the three supply voltages U, V, W of the three-phase power source may interface with a first set switches 301, 302, 303, and further interface with a second set of switches 311, 312, 313. Each set of switches may be connected in series to the three-phase power.

The motor control arrangement may be utilized to control two motors with a single power source and controller. Such arrangement may be advantageous for devices that include two motors, such as the HVAD® Pump manufactured by HeartWare Inc. in Miami Lakes, Fla., USA. The HVAD® Pump is further discussed in U.S. Pat. No. 8,512,013, the disclosure of which is hereby incorporated herein in its entirety. The "sensorless" BLDC motors do not include a hall-effect sensor for detecting rotor position. Instead, rotor position may be inferred by a control circuit based on a sensed back electromotive force (BEMF) produced by the motor windings. The BEMF effectively appears as a voltage (hereinafter, BEMF voltage) in series with and opposing the originally applied voltage. Since the rotational speed of the rotor is proportional to the BEMF, motor speed may be inferred from the BEMF voltage.

Figure 3:
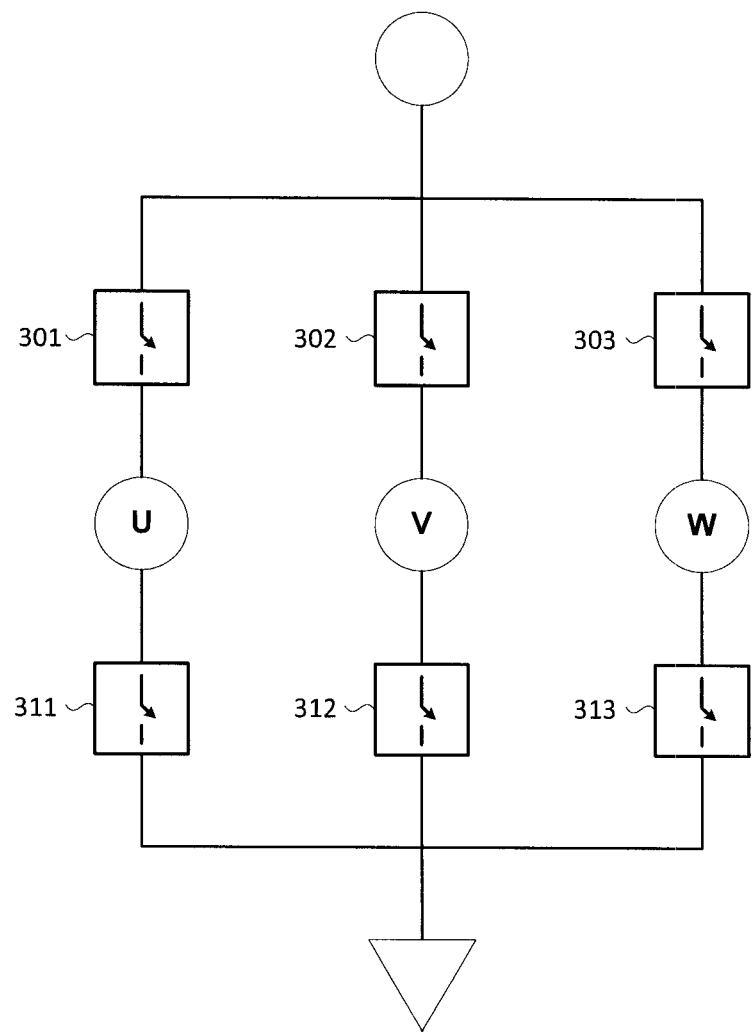
FIG. 3 is a circuit diagram of exemplary switches of the exemplary stator shown in FIG. 1.

Furthermore, rotor speed and position may be inferred from a zero-crossing of the sensed BEMF voltage (e.g., midpoint between "high" and "low" phase states of the motor windings). Zero-crossings occur at each stator during the "floating" state of the trapezoidal drive. During the zero crossing, the rotor is known to be perpendicularly orientated relative to the axis of the winding in which the sensed BEMF (or at that instant, lack of BEMF) is induced. Speed of the motor may further be deduced based on the amount of time between detected zero-crossings. For instance, in the example configurations shown in FIGS. 1 and 3, every three detected zero-crossings corresponds to a single revolution of the motor; thus, the motor speed (in RPM) is equivalent to the number of zero-crossings detected per minute, divided by three. Control of the BLDC motor may involve one or more alternative techniques (as compared to BEMF detection) for determining rotor position and motor speed.

Figure 4:
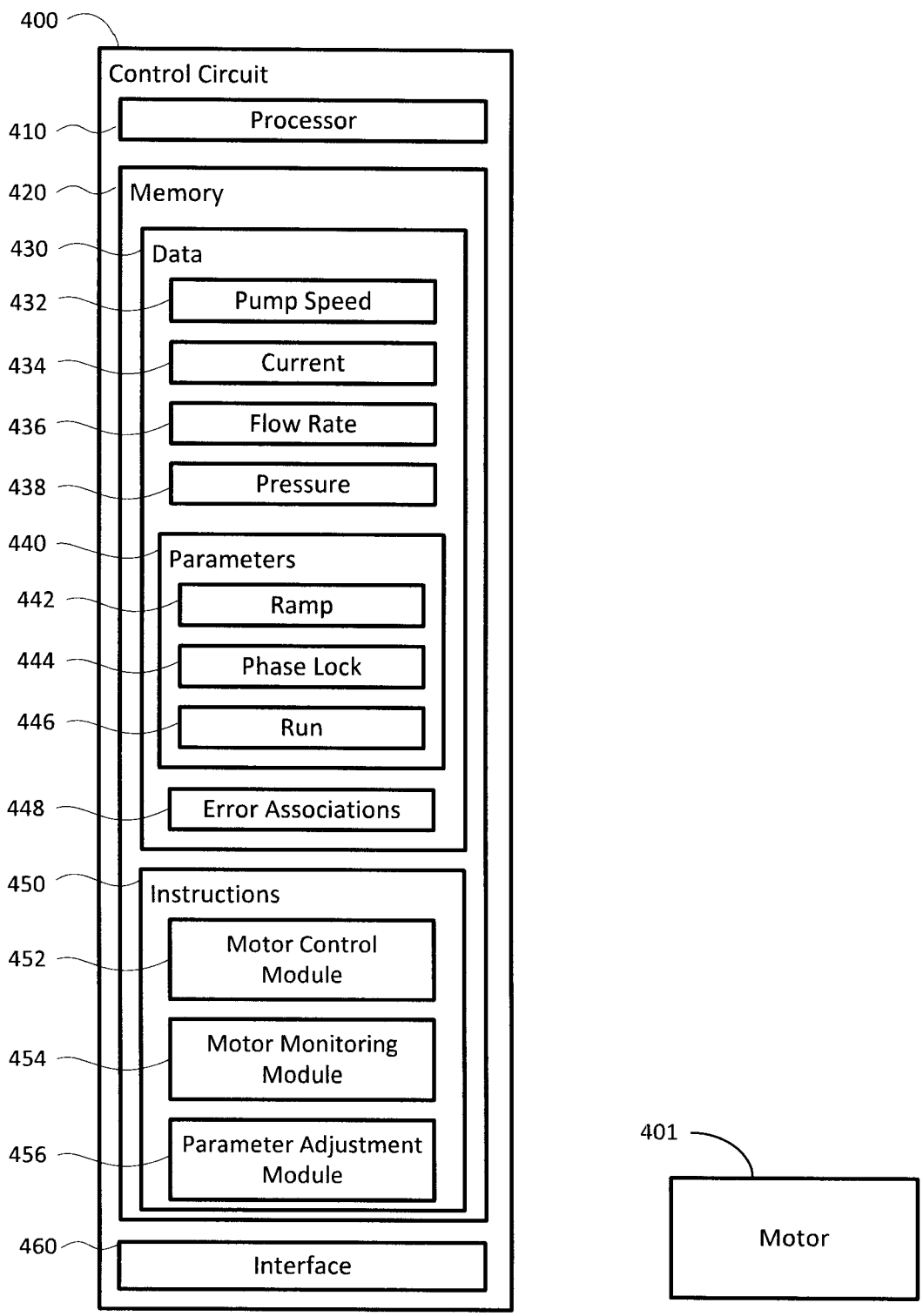
FIG. 4 is an example control circuit configured to monitor and control startup and subsequent operation of an exemplary motor of the present application.

Now referring to FIG. 4 in which an exemplary control circuit 400 capable of monitoring and controlling startup and subsequent operation of a motor 401 is illustrated according to the routines of the present disclosure. The control circuit 400 is implemented using a processor 410, a memory 420 and an interface 460 for interfacing with the motor 401. Memory 420 stores information accessible by processor 410, including instructions 450 that may be executed by the processor 410. The memory 420 also includes data 430 that may be retrieved, manipulated or stored by the processor 410. The memory may be of any type capable of storing information accessible by the processor 410, such as a hard-drive, memory card, ROM, RAM, DVD, CD-ROM, write-capable, and read-only memories. The processor 410 may be any well-known processor, such as commercially available processors. Alternatively, the processor 410 may be a dedicated controller such as an ASIC.

Data 430 may be retrieved, stored or modified by processor 410 in accordance with the instructions 450. The data may also be formatted in any computer-readable format such as, but not limited to, binary values, ASCII or Unicode. Moreover, the data 430 may comprise any information sufficient to identify the relevant information, such as numbers, descriptive text, proprietary codes, pointers, references to data stored in other memories (including other network locations) or information that is used by a function to calculate the relevant data.

The control circuit 400 includes hardware and software for controlling the various aspects of the operation of the motor. The control circuit 400 is coupled to the motor 401 through the interface 460 to collect at least some of data 430 from the motor 401. For example, data 430 may include an indication of motor speed 432, and an amount of current used to drive the motor 434. In addition, data 430 may include physiological data indicative of a physiological state of a patient into which the motor is implanted. Such data may be independently measured or sensed, or may be otherwise calculated or derived based on the data from motor 401. For instance, data 430 may include flow rate data 236 indicative of a flow rate of blood exiting a pump of the motor, and/or pressure data 238 indicative of pressure differential exerted by the pump. Some example methods and systems for collecting the above referenced data 432-438, as well as for collecting additional data, are provided in, for instance, commonly owned patent application Ser. Nos. 13/027,811, 13/355,297, and 14/294,448, the disclosures of which are hereby incorporated by reference herein in their entirety.

The data may further include startup parameters 440 for regulating the manner in which startup of the motor is controlled and/or monitored. The startup parameters 400 may include one or more ramp parameters 442 for executing, and/or ensuring proper execution of, an increasing or ramping of the speed of the motor 401 to a target motor speed. The startup parameters 440 may also include one or more phase lock parameters 444 for executing and/or ensuring proper execution of maintaining the target motor speed and phase locking of the motor. The startup parameters 440 may further include one or more run parameters 446 for running the motor under normal operation condition, and/or for ensuring that normal operation conditions are maintained. Examples of startup parameters are provided herein in connection with the routine of FIG. 5.

The data 430 may optionally further include preset error association information 448 indicating an association or correlation between a certain type of error occurring at the motor, for instance during startup. An error may occur when the motor fails to startup based on a preset startup sequence. Alternatively, an error may occur when the motor does startup, but is not operating in a desired manner as a result of the startup (e.g., below an intended speed). An error may also occur when the motor does start up, but an undesirable operational error or condition occurs during the startup (e.g., suction condition, high pressure condition, phase commutation error). In any of these cases, it may be desirable to adapt or otherwise adjust the startup parameters 440 in order to avoid errors during future startups.

The preset error association information may indicate a particular one or more startup parameters 440 that may be adjusted in response to a given error. For example, if the startup experiences a phase commutation error parameters relating to a rate at which the pump speed is ramped up (e.g., magnitude of ramping increments, time or commutations between ramping increments, etc.) may be adapted in response. For further example, if a suction condition occurs during startup, a final pump speed may be adjusted. In the case of a startup parameter having a numerical value, the error association information 448 may further indicate whether the associated startup parameter should be increased or decreased in response to the error (e.g., to reduce the risk of future errors). Again, taking the example of a phase commutation error, the error association information may indicate that a value for the magnitude of ramping increments be decreased, whereas the time or number of commutations between increments be increased. Alternative to the error association information, the control circuit may include preset data indicating a particular adjustment to be made to the startup parameters, regardless of the particular type of error experienced.

The instructions 450 stored in the memory 420 may include one or more instruction sets or modules, for performing certain operations in accordance with the present disclosure. One such module may be a motor control module 452 for controlling operation of the motor 401 (e.g., increasing or decreasing motor speed), such as in accordance with the startup and run routines described herein. The instructions may also include one or more motor monitor modules 454 for monitoring operation of the motor and registering an error in the case of an unwanted operation of the motor (e.g., causing or resulting a suction condition and/or high pressure condition). The instructions may further include a parameter adjustment module 456 for adaptively adjusting the parameters 440 used in controlling and monitoring the startup and run routines described herein.

Figure 5:
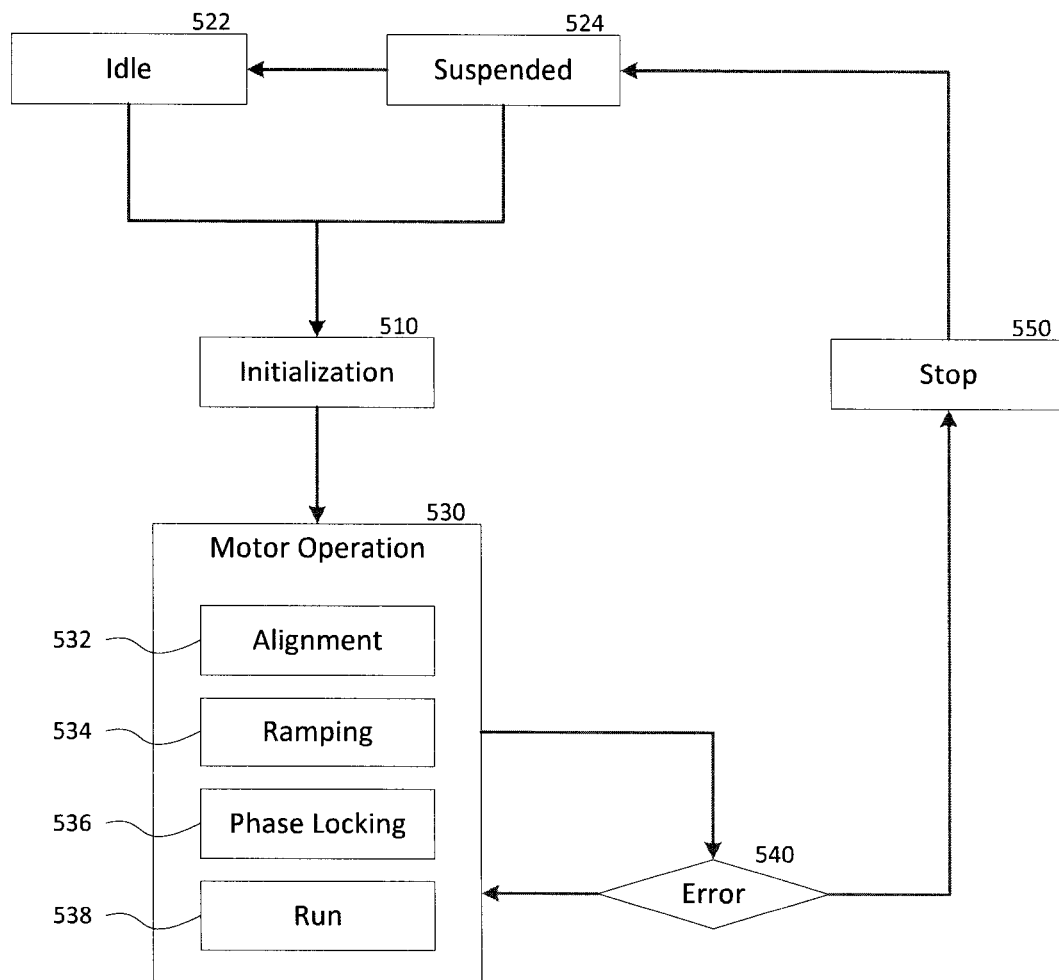
FIG. 5 is a flow chart illustrating exemplary startup routine for controlling startup of a motor constructed in accordance with the principles of the present application.

Referring now to FIG. 5, the startup routine 500 may be executed by the control circuit 400 of FIG. 4, or by a similarly capable control circuit. The routine 500 provides for initialization 510 from an idle state 522 of a motor, as well as resuming operation ("restart") from a non-idle state 524 in which control of the motor is temporarily suspended but the motor has not come to a full stop. Upon initialization 510, the control circuit enters a motor operation state 530 in which the control circuit transitions the motor to a state of normal operation. The control circuit may perform several protocols in order to bring the motor up to normal operation. The control circuit 400 performs an alignment protocol 532 in order to ascertain the rotor position at startup. As explained above, during normal operation of the motor, the rotor position may be measured based on BEMF induced by the impeller on the coils of the rotor. However, at speeds lower than normal operation range, the BEMF voltage is not enough to perform accurate rotor position sensing. Instead, a series of fixed duty-cycle pulses may be used to drive the stator coils and force the rotor into a known position. Once the rotor is "aligned" in the position forced by the pulses, the control circuit 400 may continue with bringing the motor up or back to normal operation.

Figure 6:
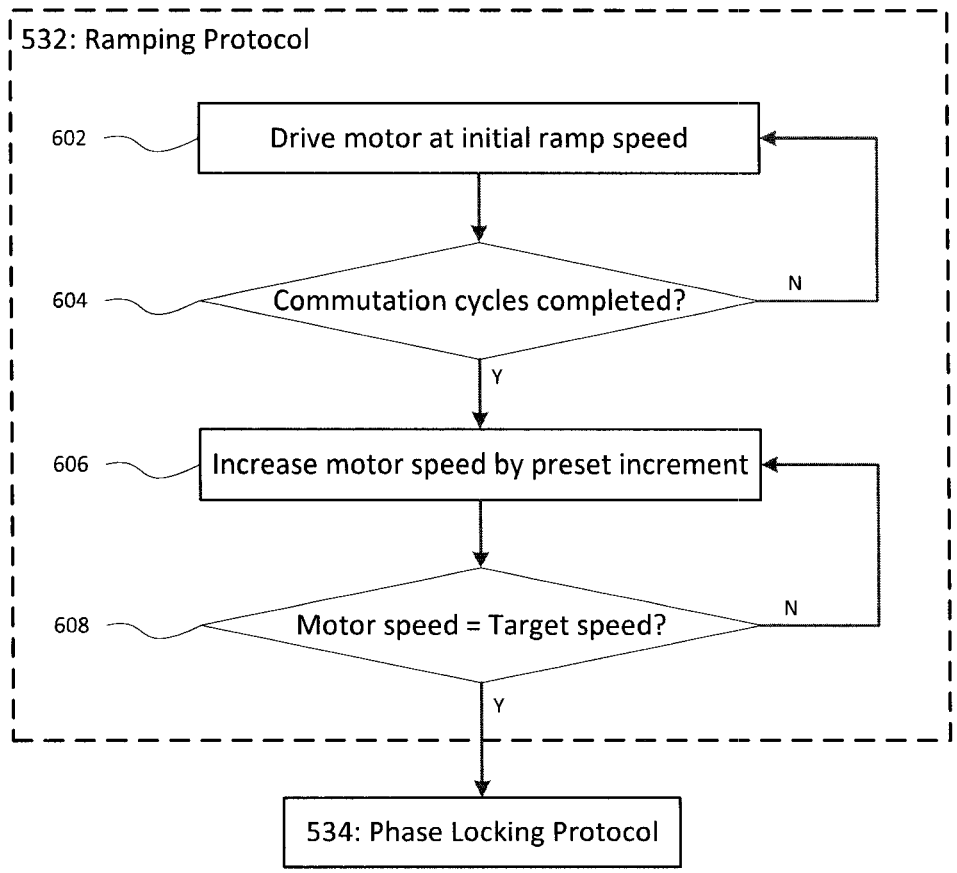
FIG. 6 is a flow chart illustrating exemplary ramping protocol for controlling startup of a motor constructed in accordance with the principles of the present application.

Referring now to FIG. 6, the control circuit 400 further performs a ramping protocol 534 in which the speed of the motor is incremented. The ramping protocol 534 begins at 602 with the control circuit 400 instructing the motor to be driven at an initial speed (e.g., about 1,000 PRM). The motor speed may be influenced by a duty cycle of the PWM power source, such that increasing duty cycle may result in a ramping of the motor speed. At 604, the control circuit 400 determines whether a preset number of commutation cycles at the initial ramp speed (e.g., about 10 cycles) have been completed. If not, the initial speed is maintained. Once the preset number of cycles is met, the ramping protocol 534 may continue at 606 by increasing the motor speed by a preset increment (e.g., 50 RPM), which may be effected by instructing the PWM power source to increase its duty cycle. At 608, the control circuit 400 determines whether the incremented motor speed is equal to a preset target motor speed (e.g., 10,000 RPM). If not, the ramping protocol 534 continues at 604 and 606 so that the motor speed may be further increased at a preset number of commutation cycles. The ramping protocol 534 may repeat this process (604, 606) until the motor is running at the target speed.

The control circuit 400 further performs a phase lock protocol 536 in which the target motor speed is maintained for a given number of commutation cycles. This ensures stability of the motor to maintain the target speed. The phase lock protocol 536 may also involve phase locking of the motor control for increased stability of the motor speed. During phase locking, the phase of the rotor may be monitored, and the motor speed may be adjusted to maintain a desired rotor phase. Phase locking may be attempted after a preset number of commutation cycles (e.g., 500). Upon completion of the alignment, ramping and phase lock protocols (532, 534, 536) without error, the control circuit transitions to a run protocol 538, in which ordinary operation of the motor commences.

During the motor operation state 530, the control circuit 400 regularly or continuously monitors operation of the motor in order to ensure that the motor is operating properly. If the control circuit fails bring the motor up to ordinary operation, or determines that the motor has ceased operating properly, the control circuit may enter an error state 540. In the error state 540, the control circuit may log the presence of a fault or error in operation of the motor. From the error state 540, the control circuit 400 may determine whether a threshold number of faults or errors have been met transition back to the particular protocol (532, 534, 536 or 538) underway prior to the fault or error. The threshold number of errors may be set differently for each specific protocol (532, 534, 536, 538). Additionally, or alternatively, an overall threshold number of errors (or density of errors) may be set for the entire normal operation state 530.

Under certain conditions, the control circuit 400 may determine that the motor needs to be stopped, temporarily or indefinitely. For instance, if the control circuit determines that a threshold number of faults or errors have been met, the control circuit may enter a stop state 500 in which the control circuit ceases driving the motor. Because the stop state 550 involves ceasing driving of the motor, the stop state is effectively a transitional step to the temporary suspension state 524. If the fault or error is eventually cleared, the temporary suspension state 524 may then transition back to an initialization state 510, so that starting or resuming normal operation of the motor may be attempted again. If the fault or error is not cleared, the motor will eventually slow to an idle, at which point the temporary suspension state 524 transitions to the idle state 522.

At either one of the error state 540 and/or stop state 550, an error notice may be generated. The error notice may include any one of a message on a visual display, a light being turned on, a message transmitted to a connected processor (e.g., via wired or wireless network) and/or an audio alert being sounded, in order to notify the subject of the control circuit's inability to successfully bring the motor to normal operation. In the case of an implantable blood pump, the error notice would in turn indicate that the pump is also not operating properly due to the motor's failure. Such a notice would inform the subject to see a clinician immediately in order restore operation of the pump.

Both control and monitoring of the motor may be based on various parameters. Some parameters may be used for controlling operation of the motor (e.g., initial motor speed, final motor speed, speed ramp increments, commutations cycles between speed increments, commutation phase ratio, gain for adjusting phase error, etc. Other parameters may be used for monitoring operation of the motor, for instance to determine the presence of a fault or error (e.g., number of consecutive zero-crossing faults that trigger an error, percentage of voltage measurements in a commutation window that are monotonic, etc.). Certain parameters may be used in both operation and monitoring, for instance monitoring an amount of error or difference from a desired point of operation (e.g., maximum commutation phase ratio error).

The following are some examples of faults and/or errors that may be monitored during the motor operation state 530:

During the ramping protocol 534, the control circuit 400 may monitor pump parameters (e.g., flow rate of blood, pump speed, pressure head, etc.) to determine a pump operation failure (e.g., due to excessive suction at the subject's ventricle). If such failure is determined (e.g., due to a drop in flow rate or excess pressure as described in commonly owned U.S. application Ser. Nos. 13/355,297 and 14/294,448, or otherwise), the ramping protocol may be stopped and the routine 500 may proceed to the stop state 550. Alternatively, the ramping protocol may continue with decreasing the motor speed until the operation failure clears (e.g., clearance of suction). Additionally, the routine may transition to the error state 440 in which an error may be logged.

During the phase lock protocol 536, the control circuit 400 may continue to monitor for errors or faults with operation of the motor as described above. Additionally, the control circuit 400 may keep track of zero-crossing faults (indicating that the motor is out of phase), or more particularly consecutive zero-crossing faults (further indicating an amount of time for which the motor is out of phase). A predetermined number of consecutive faults (e.g., 50), may result in an error being recorded at the error state 440, or in temporarily stopping, or ceasing, of operation of the motor at the stop state 550.

Similarly, prior to completing phase lock, the control circuit 400 may monitor whether the commutation phase ratio, which may be preset to a desired value (e.g., 0.3), is within a maximum error (e.g., 15%). The control circuit 400 may further use a moving average for computing the error (e.g., a weighted average using 0.2 as the weight), and a preset gain to adjusting phase error (e.g., 0.025% adjustments to duty cycle for PWM power delivered to the motor).

The control circuit 400 may further monitor whether the difference between the "floating" state voltage and the zero-crossing voltage meet a certain threshold (e.g., 2V), may keep track of whether monotonic variation between consecutive zero-crossing values is at or above a certain minimum amount (e.g., 0.01V), and may keep track of whether a minimum number of voltage measurements in a commutation window are monotonic (e.g., at least one-half of measurements). Each of these monitored parameters may be variable, such that a different moving average filter weight (e.g., 0.1), different threshold, etc., may be updated to increase the likelihood of successful phase lock.

During the run protocol 538, the control circuit 400 may continue to monitor motor operation as described above. Additionally, the control circuit 400 may monitor for variations in motor speed. In a sensorless motor, motor speed may be estimated based on the commutation phase, as explained above. A PID controller may further be used to correct such changes by adjusting the PWM duty cycle of the power provided to the motor.

Each protocol (532, 534, 536, 538) may be assigned its own set of parameters by which operation of the motor is controlled. For instance, a threshold parameter may be set differently for different protocols of the motor operation state 530, such that a given measurement may exceed a threshold parameter of one protocol (thereby triggering a fault or error), but may not exceed the threshold parameter of a different protocol (thus, not triggering a fault or error). Similarly, the number of faults or errors before which the control circuit determines to cease controlling operation of the motor may vary from one protocol to another.

Default parameters may be pre-programmed into a memory of the control circuit 400. The default parameters may further be updated automatically by the control circuit 400. For instance, if the control circuit 400 determines that a certain parameter used to control operation of the motor is causing the routine 500 to fail, the control circuit 400 may automatically adjust that default parameter in order to improve the chances of a successful startup. Such updating may occur during the error state 440 in response to a logged error, or during the stop state 450 so that the updated parameter will be used when the control circuit 400 reinitializes the startup routine 500.

Adjusting startup routine parameters may be permanent or temporary. For instance, the control circuit 400 may temporarily adjust the parameter in order to improve the chances of a successful startup of the pump, but the next time the control circuit initializes startup, the control circuit 400 may revert to the original preset parameters. Alternatively, if the control circuit 400 determines that the adjusted parameter results in a successful startup of the motor, the parameter may replace the previous default parameter, such that the next time the control circuit 400 enters the motor operation state, the control circuit 400 may initially rely on the updated parameter instead of on the default parameter.

Figure 7:
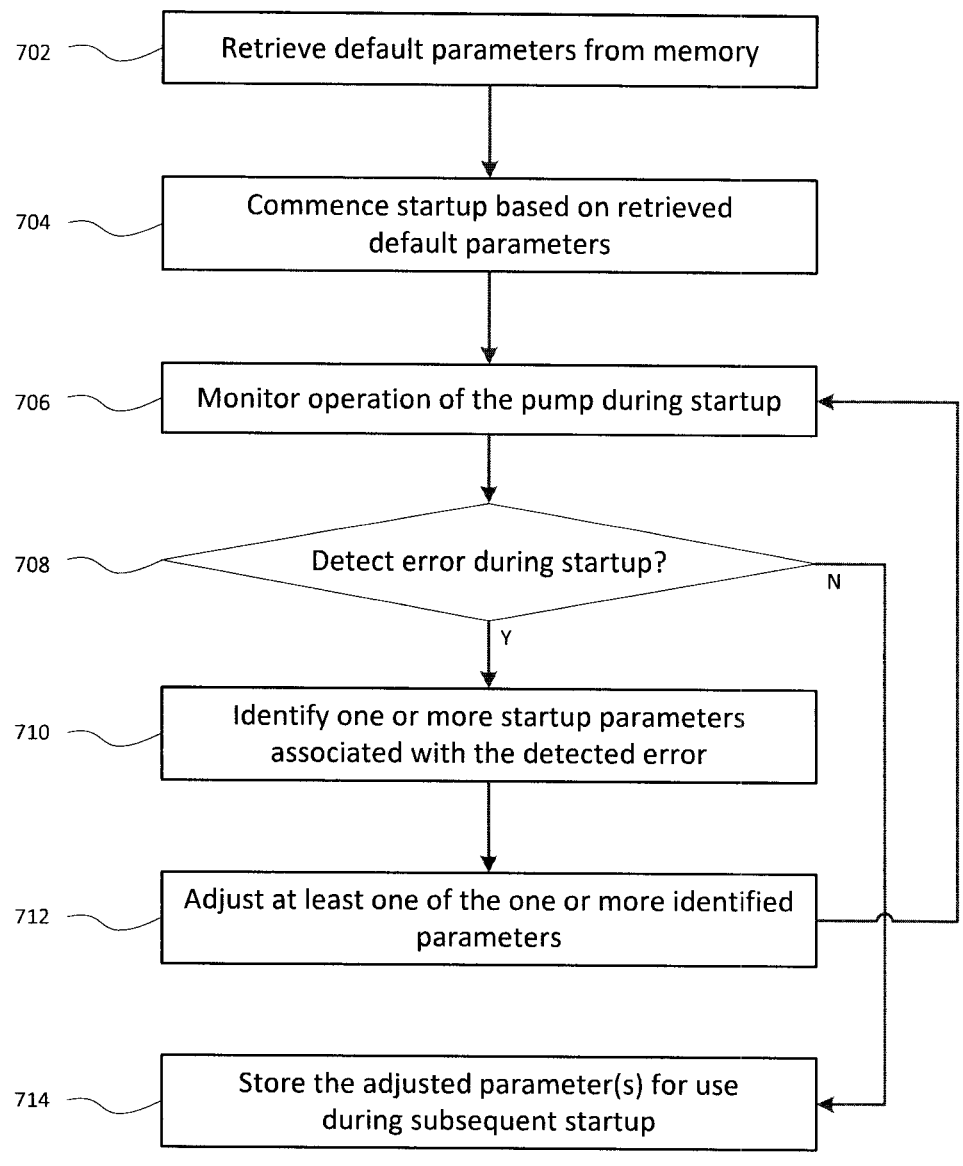
FIG. 7 is a flow chart illustrating a routine for a control circuit adapting the parameters of the startup routine shown in FIG. 5.

Now referring to FIG. 7 illustrating routine 700 for control circuit 400 adapting parameters for a startup routine, for example, routine 500 of FIG. 5, of a pump. At 702, default parameters are retrieved from a memory of the control circuit 400. The default parameters may be parameters originally input during production or development of the pump, parameters manually input (e.g., by a user of the pump or clinician evaluating the user or pump), and/or parameters that were automatically updated in a previous iteration of the routine 700.

At 704, a startup operation (such as the motor operation state 530 of FIG. 5) is commenced based on the retrieved default parameters. The retrieved default parameters may initially govern the startup operation. For example, ramping, locking, and running the pump may all be controlled based on the retrieved parameters. For further example, monitoring the pump to evaluate and/or ensure proper operation may be based on the retrieved parameters. At 706, operation of the pump during startup is monitored for errors, such that one or more pump operation errors may be detected. If, at 708, one or more errors are detected, the one or more errors may be indicative of a failure of the default parameters to startup operation the pump, such that use of the present value of that parameter (as compared to a different value for the parameter) may be decreasing the pump's likelihood of successful startup. In some cases, detection of an error may be accompanied by a specification as to the type of error detected (e.g., suction condition, commutation phase error, etc.), so that the one or more parameters associated with (e.g., potentially responsible for) the detected one or more errors may be identified at 710. Identifying parameters based on errors may be automatic, for instance, performed by a control circuit based on preset correlations between certain types of errors, and certain parameters.

Alternatively, in other cases, one or more parameters may be identified based on a predetermined adjustment routine, e.g., decrement initial speed or ramp rate if startup is unsuccessful or an error occurs during startup; increment duty cycle of PWM during initial speed operation if startup is unsuccessful or an error occurs during startup, etc. Such parameters may be "identified" (and thereby adjusted) based simply on the predetermined routine, without consideration for the type of error that has been detected.

At 712, at least one of the identified parameters is adjusted. In a similar manner that identifying a parameter based on an error may be automatic, adjustment of the parameter may be automatic, for instance, based on preset correlations that indicate whether increasing or decreasing a parameter is likely to affect an increase or decrease in the likelihood of another error registering. For instance, a parameter relating to the rate at which the speed of the pump is ramped during a ramping protocol (e.g., commutations between increments, total number of increments between start and final motor speed, etc.) may have an influence on the likelihood of an occurrence of a suction condition at the pump (e.g., for a left-ventricular assistance device (LVAD), at the patient's left ventricle near the entrance to the pump).

By adjusting such parameter or parameters to slow the rate of ramping, the likelihood of an occurrence of a suction condition may be decreased. Operations then resume at 706 with startup of the pump according to the adjusted parameters.

If startup succeeds under the adjusted parameters, and no errors are detected at 708, the routine 700 may continue at 714 with the adjusted parameters being stored in the memory. The adjusted parameters may be indicative of conditions under which startup of the pump is capable of succeeding, or possibly at least more likely to succeed than under the previous parameters. The adjusted parameters may then function as updated default parameters, such that the next time startup of the pump is initiated, the adjusted parameters may be retrieved from the memory and startup may be commenced based on the retrieved adjusted (updated default) parameters.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An apparatus for starting operation of a motor of an implantable blood pump, comprising:
   a memory storing one or more preprogrammed default parameters for at least one of controlling and monitoring the startup operation, the one or more preprogrammed default parameters including a speed of the motor; and
   a processor operatively coupled to the motor, the processor being configured to:
   commence the startup operation based on the one or more preprogrammed default parameters;
   ramp a speed of the motor based on at least one of the one or more preprogrammed default parameters, and maintain the speed of the motor for a given number of commutation cycles;
   detect an error during the startup operation, the error detected during the startup operation is indicative that the motor is operating as a result of the startup but at a rate at which the pump speed is ramped up is not normal;
   update at least one of the one or more preprogrammed default parameters to an updated parameter different than the one or more preprogrammed default parameters in response to the detected error;
   store the at least one updated parameter in the memory; and
   commence subsequent startup operations based at least in part on the at least one updated parameter.

2. The apparatus of claim 1, wherein storing the at least one updated parameter in the memory occurs when commencing subsequent startup of the motor is successful.

3. The apparatus of claim 1, wherein the memory stores parameter adjustment data indicating an association between at least one error type of the detected error and at least one associated parameter, and wherein the processor is configured to identify at least one default parameter associated with the detected error based on the parameter adjustment data and to adjust the at least one preprogrammed default parameter in response to the detected error.

4. The apparatus of claim 3, wherein the parameter adjustment data further indicates whether to at least one of increase and decrease the associated parameter in response to the at least one error type to reduce the likelihood of a recurrence of the at least one error type, and wherein the processor is configured to at least one of increase and decrease the at least one default parameter based on the parameter adjustment data.

5. The apparatus of claim 1, wherein the processor is configured to detect an error during the startup operation based on at least one of a determined speed of the motor, current supplied to the motor, flow rate of blood through the pump, and pressure head exerted by the pump.

6. The apparatus of claim 1, wherein the one or more preprogrammed default parameters includes a value indicating a threshold number of errors, and wherein the processor is further configured to cease operation of the motor in response to registering the threshold number of errors during consecutive startup operation attempts.

7. The apparatus of claim 1, wherein the one or more preprogrammed default parameters includes at least one parameter related to a rate at which speed of the motor is ramped, and wherein the processor is configured to identify a suction condition at the implantable blood pump, and to adjust the at least one parameter related to a rate at which speed of the motor is ramped in response to the suction condition.

8. The apparatus of claim 1, wherein the one or more preprogrammed default parameters includes at least one parameter related to a rate at which speed of the motor is ramped, and wherein the processor is configured to identify a high pressure condition at the implantable blood pump, and to adjust the at least one parameter related to a rate at which speed of the motor is ramped in response to the high pressure condition.

9. The apparatus of claim 1, wherein the one or more preprogrammed default parameters includes at least one parameter related to motor phase control, and wherein the processor is configured to identify a commutation error at a rotor of the implantable blood pump, and to adjust the at least one parameter related to motor phase control in response to the commutation error.

10. A method of adaptively adjusting operational parameters of a motor of an implanted medical device, comprising:
commencing a startup operation based on one or more preset operational parameters;
detecting an error during the startup operation, the error detected during the startup operation is indicative that the motor is operating as a result of the startup but at a rate at which the pump speed is ramped up is not normal;
updating at least one of the one or more preset operational parameters with an updated parameter different than one or more operation parameter in response to the detected error;
replacing at least one of the one or more preset operational parameters with the at least one updated parameter as a default parameter in the memory; and
commencing subsequent startup operations based at least in part on the at least one updated parameter.

11. The method of claim 10, wherein the detecting and updating are repeatedly performed until the startup operation is successfully completed.

12. The method of claim 11, further comprising associating the detected error with at least one of the one or more present operational parameters based upon preset association data, and wherein adjusting at least one of the one or more preset operational parameters is based on the association.

13. The method of claim 12, wherein the association further comprises an indication whether to at least one of increase and decrease the at least one of the one or more preset operational parameters, and wherein updating at least one of the one or more preset operational parameters comprises at least one of an increase and a decrease of the at least one of the one or more preset operational parameters based on the indication.

14. The method of claim 13, wherein commencing a startup operation comprises ramping a speed of the motor based on at least one of the one or more preset operational parameters, and phase-locking the motor based on at least one of the one or more preset operational parameters.

15. The method of claim 14, wherein when the motor is in an idle state, commencing a startup operation comprises aligning one or more stators of the motor with a predetermined position, and ramping a speed of the motor commences with the stators in the predetermined position.

16. The method of claim 15, wherein detecting an error during the startup operation is based on at least one of a determined speed of the motor and current supplied to the motor.

17. The method of claim 16, wherein the implanted medical device is a blood pump, and wherein detecting an error during the startup operation is based on at least one of a flow rate of blood through the pump, and pressure head exerted by the pump.

18. The method of claim 10, wherein commencing a startup operation includes applying a plurality of fixed-duty cycle pulses to the motor.

* * * * *